United States Patent

Wang et al.

[11] Patent Number: 5,423,326
[45] Date of Patent: * Jun. 13, 1995

[54] APPARATUS AND METHOD FOR MEASURING CARDIAC OUTPUT

[75] Inventors: Xiang Wang, Lansdale; Hun H. Sun, Blue Bell, both of Pa.

[73] Assignee: Drexel University, Philadelphia, Pa.

[*] Notice: The portion of the term of this patent subsequent to May 10, 2011 has been disclaimed.

[21] Appl. No.: 61,360

[22] Filed: May 14, 1993

Related U.S. Application Data

[63] Continuation-in-part of Ser. No. 61,793, May 13, 1993, which is a continuation-in-part of Ser. No. 834,425, Feb. 12, 1992, Pat. No. 5,309,917, which is a continuation-in-part of Ser. No. 758,034, Sep. 12, 1991, abandoned.

[51] Int. Cl.⁶ .................................................. A61B 5/04
[52] U.S. Cl. .................................... 128/713; 128/693; 128/734
[58] Field of Search ............................... 128/670–672, 128/693–696, 700, 713, 687, 734

[56] References Cited

U.S. PATENT DOCUMENTS

| | | |
|---|---|---|
| Re. 30,101 | 9/1979 | Kubicek et al. |
| 3,340,867 | 9/1967 | Kubicek et al. |
| 3,452,743 | 7/1969 | Rieke |
| 3,730,171 | 5/1973 | Namon |
| 3,742,936 | 7/1973 | Blanie et al. |
| 3,835,839 | 9/1974 | Brown |
| 3,835,840 | 9/1974 | Mount |
| 3,871,359 | 3/1975 | Pacela |
| 3,874,368 | 4/1975 | Asrican |
| 3,882,851 | 5/1975 | Sigworth |
| 3,976,052 | 8/1976 | Junginger et al. |
| 3,994,284 | 11/1976 | Voelker |
| 3,996,925 | 12/1976 | Djordjevich |
| 4,137,910 | 2/1979 | Murphy ........................ 128/713 X |
| 4,305,400 | 12/1981 | Logan |
| 4,361,049 | 11/1982 | Volgyesi ........................ 128/713 X |
| 4,422,458 | 12/1983 | Kravath |
| 4,437,469 | 3/1984 | Djordjevich et al. |
| 4,450,527 | 5/1984 | Sramek |
| 4,562,843 | 1/1986 | Djordjevich et al. |
| 4,641,260 | 2/1987 | Fukukita et al. |
| 4,676,253 | 6/1987 | Newman et al. |
| 4,757,824 | 7/1988 | Chaumet |
| 4,807,638 | 2/1989 | Sramek |
| 4,862,361 | 8/1989 | Gordon et al. ................ 128/661.04 |
| 4,870,578 | 9/1989 | Vysin et al. |
| 4,979,110 | 12/1990 | Albrecht et al. |
| 5,025,784 | 6/1991 | Shao et al. |
| 5,046,504 | 9/1991 | Albert et al. |
| 5,101,828 | 4/1992 | Welkowitz et al. |
| 5,103,828 | 4/1992 | Sramek |
| 5,109,862 | 5/1992 | Kelen et al. |
| 5,178,151 | 1/1993 | Sackner |
| 5,178,154 | 1/1993 | Ackmann et al. |
| 5,309,917 | 5/1994 | Wang et al. ................ 128/713 X |

FOREIGN PATENT DOCUMENTS 2823880 10/1979 Germany .......................... 128/713

OTHER PUBLICATIONS

Kizakevich et al, "Continuous Noninvasive Cardiac Monitoring etc.", Proc. Symp. on Computers in App. Med. Care, 1977 pp. 325–336.

(List continued on next page.)

Primary Examiner—Lee S. Cohen
Assistant Examiner—Jeffrey R. Jastrzab
Attorney, Agent, or Firm—William H. Eilberg

[57] ABSTRACT

The present invention reliably computes cardiac output with a noninvasive procedure. The system measures the electrical impedance of a patient's body, during a time interval of interest. The system then obtains frequency transforms of various time segments of the first derivative of the impedance signal. Each such transform is integrated over a frequency range of interest, and the values of the integrals are plotted as a function of time. The graph so derived has characteristic extrema which can be used to identify critical points in the impedance derivative signal. These critical points can be used to determine parameters which are used in a calculation of stroke volume and cardiac output.

12 Claims, 5 Drawing Sheets

OTHER PUBLICATIONS

Kizakevich et al, "an Automated System for Systolic Time Interval Analysis", Proc. Dig. Eq. Comp. Users Soc., 1976, pp. 795–798.

Gollan et al, "Continuous Electrode Monitoring etc.", British Heart Journal, 1978, pp. 1390–1396.

Geddes, "The Measurement of Cardiac Output and Blood Flow", from Cardiovascular Devices and their Applications, pp. 100–135.

Sramek, "Electrical Bioimpedance", 1983, pp. 95–105.

Miyamoto et al, "Continuous Determination of Cardiac Output etc.", Med. & Biol. Eng. & Computing, 1981, pp. 638–644.

Miyamoto et al, "Automatic Determination of Cardiac Output etc" Proc. 5th Int'l Conf. on Electr. Bio-Impedance, 1981, pp. 45–48.

Miyamoto et al, "Automatic Determination of Cardiac Output etc" Biotelemetry Patient Monitoring, 1981, pp. 189–203.

Sramek et al, "Stroke Volume Equation etc.", Proc. 6th Int'l Conf. on Electr. Bioimpedance, 1983, pp. 1–2.

Sramek, "Cardiac Output by Electrical Impedance", 1982, pp. 93–97.

Sramek, "Noninvasive Technique for Meas. of Cardiac Output etc" Proc. 5th Int'l Conf. on Electr. Bioimped., 1981, pp. 39–42.

Kubieck et al, "Development and Evaluation of an Impedance Cardiac Output Sys.", Aerospace Medicine, 1966, pp. 1208–1212.

Kubicek et al, "the Minnesota Impedance Cardiograph-Theory and Applications", Biomed. Eng. 1974, pp. 410–416.

APPARATUS AND METHOD FOR MEASURING CARDIAC OUTPUT

CROSS-REFERENCE TO PRIOR APPLICATIONS

This is a continuation-in-part of the application Ser. No. 08/061,793 of Xiang Wang and Hun H. Sun entitled "System and Method of Impedance Cardiography Monitoring", filed May 13, 1993, which is a continuation-in-part of application Ser. No. 07/834,425, filed Feb. 12, 1992 now U.S. Pat. No. 5,309,917, which is a continuation-in-part of application Ser. No. 07/758,034, filed Sep. 12, 1991, now abandoned. The present application hereby incorporates by reference the disclosures of all of the above-identified applications.

BACKGROUND OF THE INVENTION

The present invention relates to impedance cardiography. Impedance cardiography is a method of using the measured electrical impedance of the body to determine cardiac output.

When electrodes are connected at two locations on the human body, and an alternating electric current is made to flow through the body, from one electrode to the other, one finds that the body has a measurable impedance which varies with time. If the electrodes are placed such that the current flows through the thorax, the changes in impedance result from changes in the amount of blood flowing in the vessels in the region between the electrodes. In general, the effective impedance of the portion of the body between the electrodes varies inversely with the amount of blood in these vessels. Thus, in theory, one can determine the amount of blood in the thoracic vessels, at a given time, from a measurement of electrical impedance of the body. Such impedance is called "bioimpedance" because it comprises impedance of a set of biological tissues.

The instantaneous amount of blood in the vessels is directly related to the performance of the heart. When blood is pumped out of the heart, the vessels in the thorax become momentarily filled with blood, and the impedance in the thorax decreases rapidly. After the ventricular contraction is complete, the impedance increases to its former level. Analysis of bioimpedance can therefore provide information on cardiac output.

Other investigators have developed mathematical models which express cardiac output as a function of certain parameters which can be derived from measurements of bioimpedance. Examples of such models are found in Re. U.S. Patent No. 30,101 (Kubicek) and U.S. Pat. No. 4,450,527 (Sramek). The disclosures of both of the above-cited patents are incorporated by reference into this specification. The Sramek patent also describes another model published by Kubicek in 1974, after the issuance of the original Kubicek patent. Both the model disclosed by the Sramek patent, and the model developed by Kubicek in 1974 require measurement of two critical parameters to determine stroke volume (and hence cardiac output). The first parameter is the maximum excursion of the first derivative of the impedance signal, starting at a time corresponding to the opening of the aortic valve. The second parameter is the ventricular ejection time (VET), which is equivalent to the time interval between the opening and subsequent closing of the aortic valve.

The technique of using bioimpedance measurements to determine cardiac output has great allure, because it enables the physician to obtain important information on heart function with an entirely noninvasive procedure. Alternative methods of determining cardiac output require heart catheterization, which carries an inherent risk, and which is relatively expensive.

Unfortunately, the bioimpedance techniques of the prior art have not been very successful in reliably measuring cardiac output. The primary problem with bioimpedance measurements is separating the "true" signal from spurious signals, or "artifacts". For example, the breathing of a patient is known to affect the impedance profile of the body. Some investigators have suggested taking impedance measurements while the subject briefly stops breathing. Obviously, the latter solution is not desirable and not usually very practical. Others have suggested taking an arithmetic average of several measurements to compensate for the so-called respiratory artifact. This averaging technique has not yielded satisfactory results. Still others have proposed ensemble averaging techniques which include superimposing a plurality of waveforms and obtaining information from a derived "average" waveform. But ensemble averaging techniques are not valid if the underlying signal is not strictly periodic.

In general, it is very difficult to analyze the signal representing the derivative of impedance. Various artifacts mask the critical features of this signal, and there has been no easy method of reliably extracting from the impedance signal the information needed for calculation of cardiac output.

The present invention provides an improved method and apparatus for measuring cardiac output, and overcomes the problems described above. The method of the present invention provides a reliable means of deriving meaningful data from bioimpedance measurements, while eliminating the effects of artifacts in the impedance signal.

SUMMARY OF THE INVENTION

In brief, the method of the present invention includes deriving a graph which contains an unambiguous pattern of extreme points, which graph can be used to identify the critical points in the impedance derivative signal necessary for calculation of cardiac output.

According to this method, one first obtains a measurement of thoracic impedance, during a time interval of interest. From this impedance measurement, one derives a signal representing the first derivative of the impedance signal. Next, one divides the above-mentioned time interval of interest into a large number of short time intervals. For each such short time interval, one computes a frequency transform (such as a Fourier transform, a Fast Fourier transform, or the like), each frequency transform being capable of being represented by a graph showing power or intensity as a function of frequency. All of the frequency transforms can be assembled into one three-dimensional graph which relates time, frequency, and intensity.

Next, one converts the three-dimensional graph into a two-dimensional graph, in the following manner. For each point in time, one computes a definite integral of the frequency transform over a frequency range of interest. Each such definite integral yields a number which is plotted against time. The resulting two-dimensional graph contains unambiguous extrema which form a recognizable and repeating pattern. The two-dimensional graph is then compared with a graph of the signal representing the first derivative of impedance. One can use the extrema from the above-described two-dimensional graph to identify the critical points on the impedance derivative signal, which critical points define parameters which are used in making an accurate calculation of cardiac output.

The above-described method is preferably implemented with a digital computer, so that the impedance signal can be quickly analyzed and the results obtained in real-time.

The present invention therefore has the primary object of providing an improved method and apparatus for performing impedance cardiography.

The invention has the further object of providing a method and apparatus which overcomes the problem of interpreting an impedance signal in the presence of noise or artifacts in the signal.

The invention has the further object of improving the accuracy and reliability of impedance cardiography.

The invention has the further object of providing a reliable, accurate, and entirely noninvasive technique for measuring cardiac output.

The reader skilled in the art will recognize other objects and advantages of the invention, from a reading of the following brief description of the invention, the detailed description of the invention, and the appended claims.

DETAILED DESCRIPTION OF THE INVENTION

The essence of the method of the present invention is the derivation of a graph which unambiguously locates certain critical points on an impedance derivative signal, which critical points enable the computation of cardiac output. The latter graph, produced by the steps outlined below, virtually eliminates artifacts from the impedance derivative signal.

The first step in the method of the present invention is to measure thoracic impedance. The measurement can be done in any conventional manner, and the details of such measurement will be known to the reader skilled in the art. The result of the measurement is a signal representing thoracic impedance as a function of time, over a time interval of interest. The interval of interest usually begins at or before the beginning of a stroke of the heart and ends after the stroke is completed.

Figure 1:
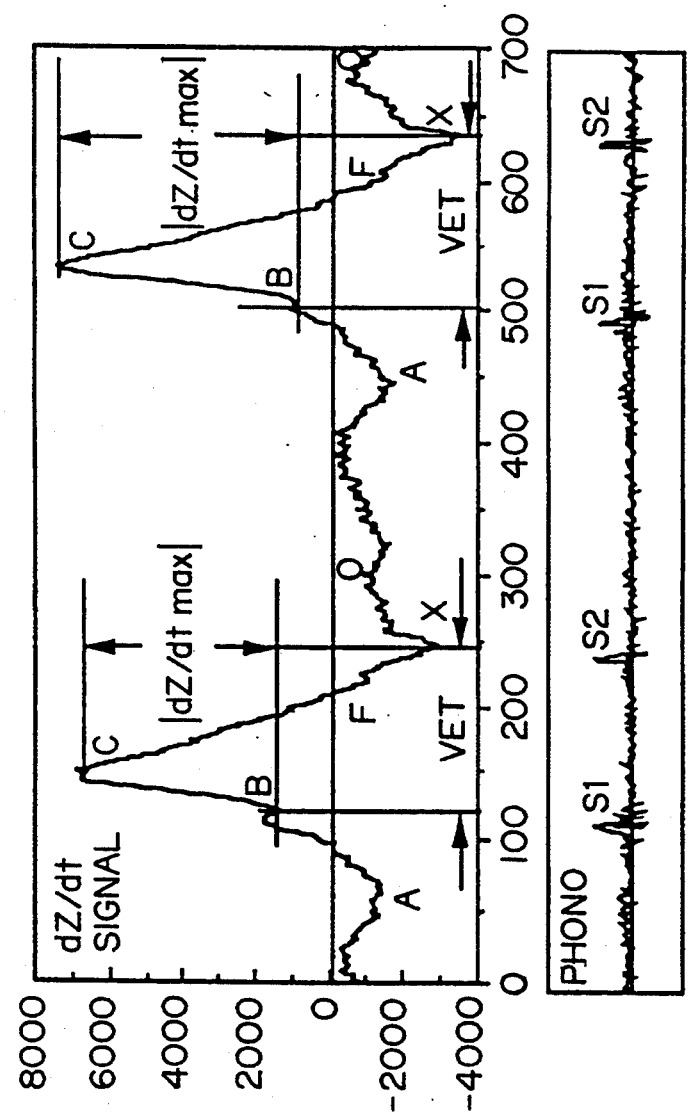
FIG. 1 provides a graph showing a typical signal representing the inverted first derivative of thoracic impedance of a patient.

The next step is to differentiate the impedance signal with respect to time. FIG. 1 shows a graph of a signal representing the first derivative of the impedance. When the aortic valve opens, and blood fills the vessels in the thorax, the electrical impedance rapidly decreases. Thus, the major excursion of the impedance derivative signal is negative. For convenience of interpretation, it is customary to change the sign of the impedance derivative, to create a positive-going signal. Thus, FIG. 1 shows the negative of the impedance derivative signal. The vertical distance from point B to point C is called $|(dZ/dt)_{max}|$. Whether one uses the impedance derivative signal, or the negative of the impedance derivative signal (as shown in FIG. 1) does not significantly affect the method of the present invention, or the apparatus used to practice the method. In FIG. 1, the units on the vertical axis are arbitrary. The units on the horizontal axis are such that 500 units equal one second. Of course, the scale can be changed. The graph below the graph of the impedance signal in FIG. 1 represents heart sounds, and will be discussed later.

The impedance derivative signal has certain characteristic points, represented by the letters A, B, C, F, X, and O in FIG. 1. Point B corresponds to the moment at which the aortic valve opens, and point X corresponds to the closing of that valve. The excursion of the signal from point B to point C ($|(dZ/dt)_{max}|$) comprises the change in the impedance derivative signal from the time of opening of the aortic valve to the time at which the impedance derivative is at a minimum. The time between point B and point X represents the ventricular ejection time (VET). As noted above, $|(dZ/dt)_{max}|$ and VET are the parameters necessary to calculate stroke volume, and hence cardiac output, in the models described by Kubicek and Sramek.

As explained above, the above-described parameters are usually not apparent from observation of the impedance derivative signal. Artifacts in the signal, due to breathing, motion, noise, or other factors, obscure the basic information contained in the signal. Such artifacts may make it difficult or impossible, for example, to determine when the maximum impedance excursion occurs, or when the ventricular ejection period occurs. The present invention therefore performs the following steps to extract the desired information.

Figure 2:
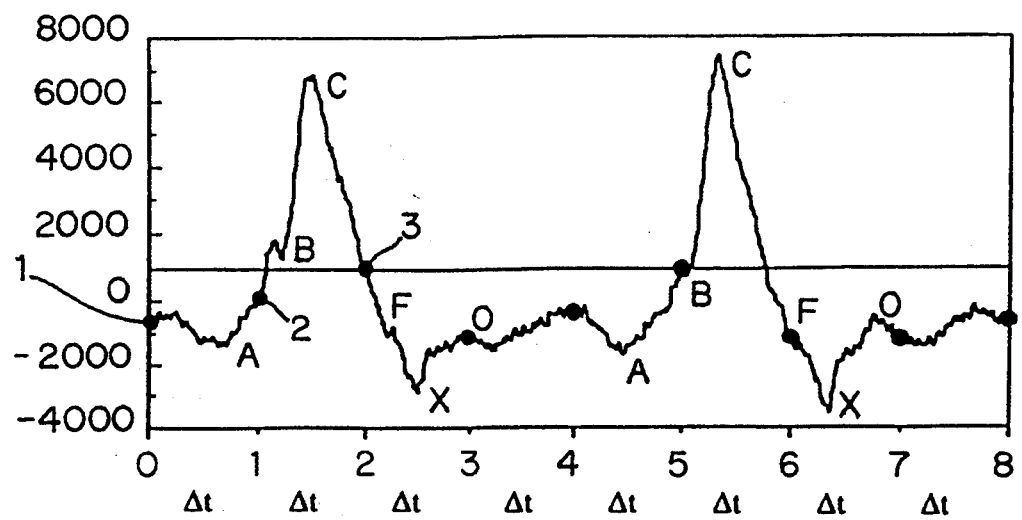
FIG. 2 provides a graph showing the division of the impedance derivative signal into a plurality of segments corresponding to small intervals of time.

First, as indicated symbolically in FIG. 2, the time domain of the impedance derivative signal is divided into a large number of segments Δt, each having a finite width. In general, Δt is at least an order of magnitude less than the time domain of the impedance derivative signal (which is of the order of magnitude of the time required for one heartbeat). Next, one derives a frequency transform for each corresponding segment of the impedance derivative signal, for each indicated segment of time.

For example, in FIG. 2, one considers the function comprising the line extending from point 1 to point 2, with the remainder of the function equal to zero. One then computes a frequency transform of that function. One would then consider the function defined by the line extending from point 2 to point 3, over the time interval Δt to 2*Δt, with the function equal to zero for all other intervals, and would obtain a similar transform. One repeats this process, isolating each finite segment of the impedance derivative signal and computing the frequency transform for each segment.

Instead of computing the frequency transform for non-overlapping short time intervals, as discussed above, one could instead use overlapping intervals. The latter method is preferred because it increases the resolution of the process, and thus improves the reliability of the results. In using overlapping intervals, one "moves" the short time interval of interest by a small amount, which amount is less (or substantially less) than the width of the interval itself, until transforms have been computed for segments covering the entire underlying function. The use of overlapping intervals tends to compensate for the fact that each interval must have a nonzero width.

The term "frequency transform" is intended to include all mathematical procedures which convert a given function of time into a function of power or energy versus frequency. The basic transform of this kind is the Fourier transform, or the Fast Fourier transform, but many other kinds of similar transforms have been developed in the field of applied mathematics. The important common feature of such transforms is that they are functions which relate power (or energy) to frequency. Such transforms show the relative power or intensity of each frequency component of an underlying signal.

Figure 3:
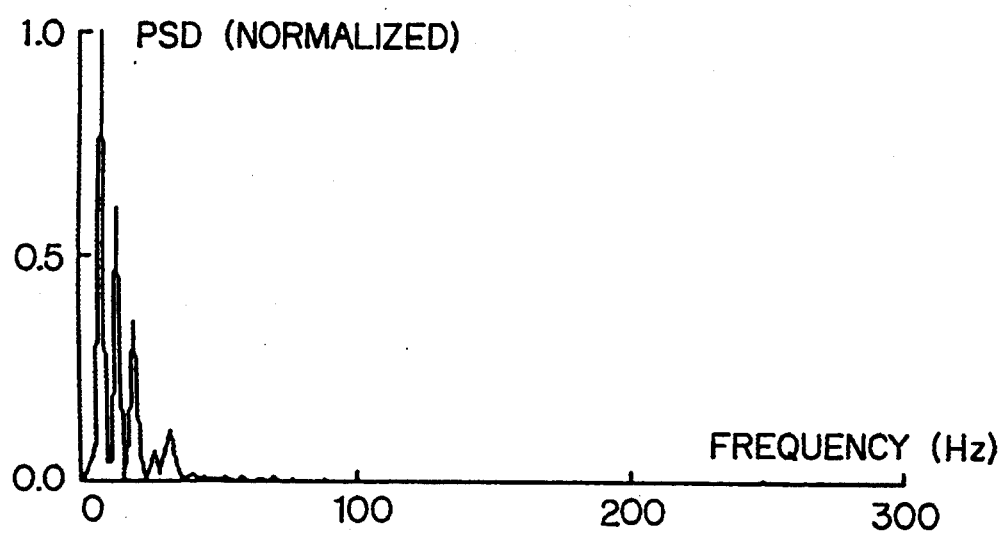
FIG. 3 provides a graph showing a hypothetical frequency transform of the impedance derivative signal, taken for a particular short interval of time.

FIG. 3 represents a hypothetical frequency transform, taken for one of the time intervals of the signal shown in FIG. 2. In FIG. 3, the abscissa is frequency and the ordinate is power, which is equivalent to intensity. It is important to remember that the function shown in FIG. 3 represents the frequency transform of a signal comprising just one small piece of the signal of FIG. 2, with the remainder of that signal momentarily set to zero. The vertical axis of FIG. 3 is labeled PSD, for "power spectrum density". The values on the vertical axis are normalized so that the maximum value is unity.

Note that the frequency transform is said to be taken at one particular time. Actually, as explained above, each frequency transform is computed for a segment of the impedance derivative over a finite interval of time, i.e. an interval having a nonzero width. The single "time" associated with a particular frequency transform can be defined as the beginning, the end, the middle, or some other point in the short time interval. As long as the latter definition is applied consistently for each such transform, the method will be valid.

Figure 4:
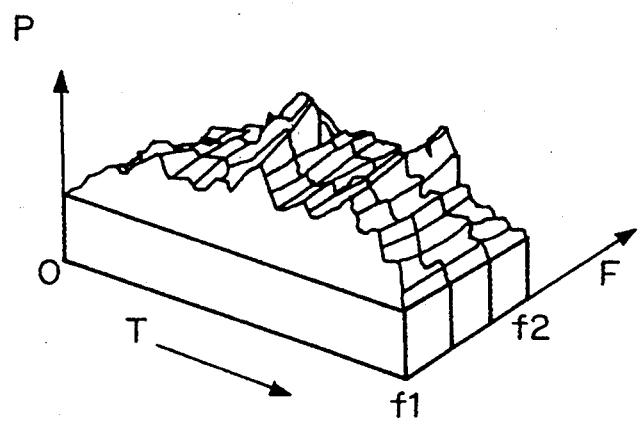
FIG. 4 shows a portion of a three-dimensional graph derived by assembling a plurality of frequency transforms of the type shown in FIG. 3.

As noted above, one computes the frequency transform for each segment of the impedance derivative signal. One can present the results in the form of a three-dimensional graph showing power as a function of frequency and time. A portion of such a graph is shown in FIG. 4. This graph is sometimes called a "spectrogram". One can best understand the spectrogram by visualizing "slices" of the function taken at particular moments in time. For each such "slice", the function becomes a two-dimensional graph of power versus frequency, similar to the frequency transform shown in FIG. 3.

The next step is to produce a two-dimensional graph from the three-dimensional spectrogram, in the following manner. For each value of time, one computes a definite integral of the power versus frequency function, over a finite range of frequencies. The value of this definite integral becomes the ordinate, and the corresponding value of time is the abscissa. In computing each definite integral, the limits of integration comprise a range of frequencies of interest. Frequencies lying outside this range are ignored.

Figure 5:
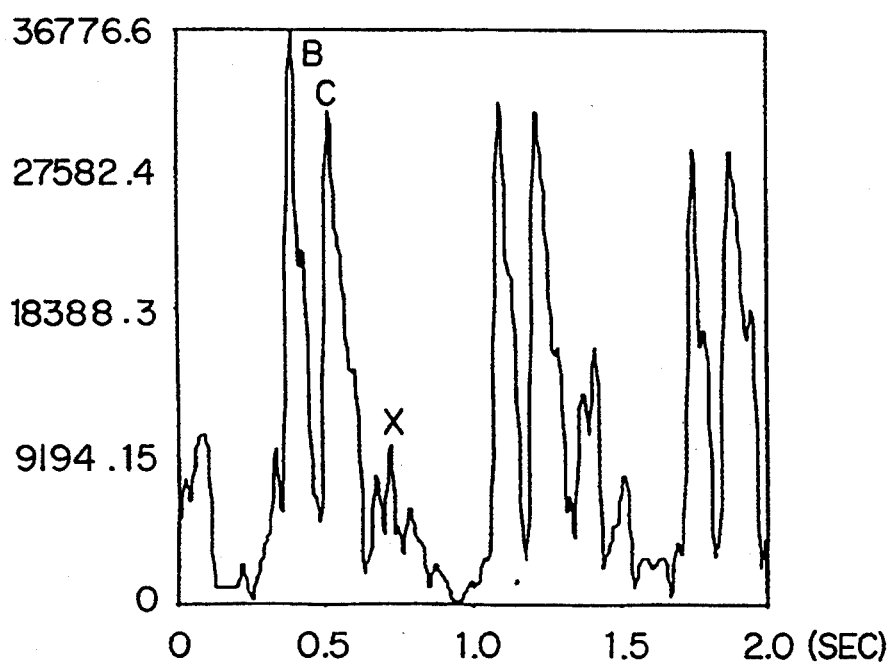
FIG. 5 shows a two-dimensional graph derived from the three-dimensional graph of FIG. 4, the two-dimensional graph being used to interpret the relevant portions of the impedance derivative signal.

By assembling the results of the above-described process, one obtains a two-dimensional graph. A hypothetical result is shown in FIG. 5. The horizontal axis represents time, while the vertical axis is a scale representing the value of the definite integrals described above. One is not concerned with the dimensions of the definite integrals; rather, one is concerned only with the pattern defined by the two-dimensional graph. Thus, one may scale the values of the ordinates, so that they fit conveniently on the graph.

What is important about the graph of FIG. 5 is that it shows a repeating and unambiguous pattern of extrema. In FIG. 5, one observes a pattern having two sharp peaks, the first peak being higher than the second, followed by a group of shorter peaks. The first two peaks of each pattern are labeled B and C in FIG. 5. The next highest peak is labeled X. The designations B, C, and X correspond to similarly labeled points of FIG. 1. It turns out that the points B, C, and X correspond exactly to the times at which points B, C, and X of FIG. 1 occur. Thus, by comparing a graph similar to FIG. 5, with the impedance derivative signal similar to FIG. 1, one can locate the points B, C, and X, and thus can deduce valuable information about the impedance derivative signal.

More specifically, one can note the times at which points B and C occur in FIG. 5, and can mark off these times on the graph of FIG. 1. The difference between the value of the impedance derivative at point B and its value at point C is the maximum impedance derivative, which is one of the parameters used in calculating cardiac output. Similarly, by noting the time at which point X occurs in FIG. 5, and by marking this time on the graph of FIG. 1, one can directly compute the time between points B and X, which is the ventricular ejection time (VET), which is also needed in the models discussed above.

Thus, the present invention produces a two-dimensional graph, derived by integrating various frequency transforms of the impedance derivative signal, over a frequency range of interest, and compares that graph with the impedance derivative signal to identify significant points of that signal. Knowledge of the significant points of the impedance derivative signal is sufficient to compute stroke volume and cardiac output. Cardiac output is computed by multiplying the stroke volume by the heart rate.

In the explanation given above, it was assumed that time began at some arbitrary zero value. In practice, it is desirable to know when to start the analysis. Failure to begin the analysis at an appropriate time could lead to erroneous results, because one might mistakenly focus on an entirely irrelevant portion of the impedance derivative signal. Thus, one preferably uses a conventional electrocardiogram (EKG) signal to determine the time over which the impedance signal will be measured. The EKG signal has well-known and recognizable features. One can monitor the EKG and activate the impedance measuring equipment upon detection of a selected portion of the EKG. Note, however, that the EKG itself plays no direct role in the computation of stroke volume according to the present invention. However, since a calculation of cardiac output requires knowledge of the heart rate, one could use the EKG signal to determine heart rate. But other means of measuring heart rate could be used instead, and one could also provide some alternative means of timing the start of the analysis, so the EKG signal is not absolutely necessary to the practice of the present invention.

Consideration must be given to the frequency range of interest, over which the frequency transforms will be integrated. It turns out that the frequency range of interest is approximately 30–55 Hz. The latter range can be determined empirically by analyzing impedance signals from many patients. One can approximately identify the portions of the impedance signals which contain the events of interest (i.e. the opening and closing of the aortic valve) by comparing the impedance signal with an observed pattern of heart sounds, or with an EKG. The bottom portion of FIG. 1 shows a graph (called a "phonocardiogram") representing typical sounds made by the heart. Note that the discernible sound spikes are well-correlated with points B and X on the impedance derivative signal, i.e. with the opening and closing of the aortic valve.

By computing a frequency transform over the portions of the impedance signal containing the events of interest, one can determine what frequencies account for most of the power in the signal. Note that the frequency range of 30–55 Hz is considered constant, and is applied consistently throughout each iteration of the method, in computing the definite integrals of the frequency transforms.

The phonocardiogram is not practical for routine use in determining stroke volume because it is very sensitive to noise and it requires sensors which are difficult to attach reliably to the human body. The present invention could use the phonocardiogram as a one-time means of determining the frequency range of interest. But the phonocardiogram is not a practical substitute for the method of the present invention.

Figure 6:
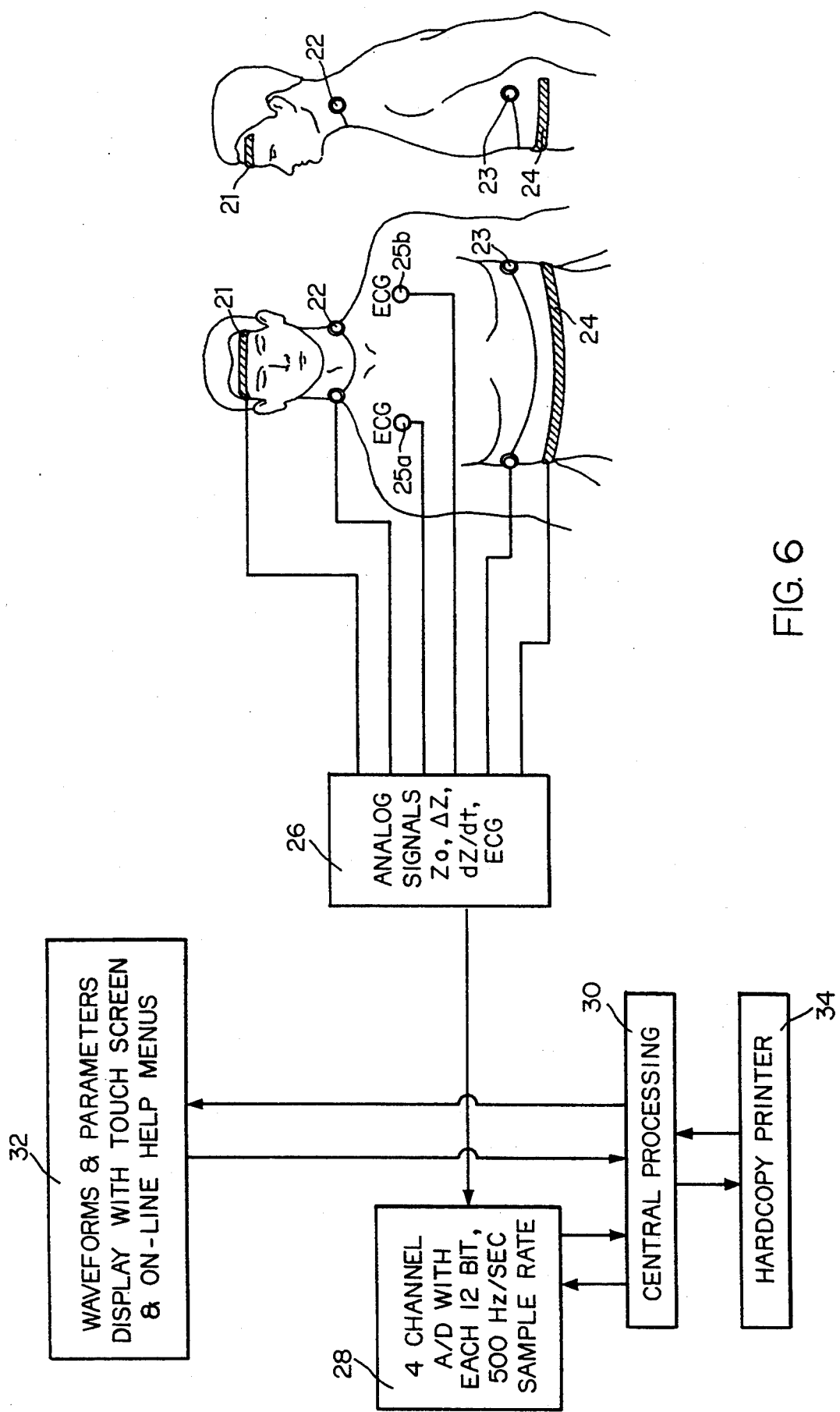
FIG. 6 provides a block diagram of the apparatus made according to the present invention, and includes front and side views of a patient.

FIG. 6 provides a block diagram of the apparatus which can be used to practice the present invention. The system of FIG. 6 includes an outer pair of electrodes 21 and 24 and an inner pair of electrodes 22 and 23. Electrode 21 is a strip electrode; electrode 24 is a band electrode. Electrodes 22 and 23 are spot-type skin electrodes. Electrodes 21 and 24 could instead be a pair of spot electrodes; the present invention can be practiced with varying arrangements. Electrodes 25a and 25b are conventional EKG electrodes.

The electrodes are connected to a signal generation and pickup device 26. Device 26 generates a voltage which is applied to the body. Device 26 also includes means for measuring the various electrical parameters of interest. As indicated on FIG. 6, the pickup device can measure the base electrical impedance of the thorax $Z_o$, the change in impedance $\Delta Z$, the derivative of impedance with respect to time (dZ/dt), and the electrocardiogram. The pickup device is connected to an analog-to-digital converter 28, the output of which is connected to processor 30. Processor 30 can be a microprocessor, or any equivalent computing device. Processor 30 is connected to display 32 and to printer 34.

The arrangement shown in FIG. 6 is only exemplary and not limiting. Other arrangements and numbers of electrodes can be used. The peripheral devices used with the processor can also be varied within the scope of the invention. What is necessary is that a means be provided for measuring bioimpedance and for performing calculations based on the measured signals.

Figure 7:
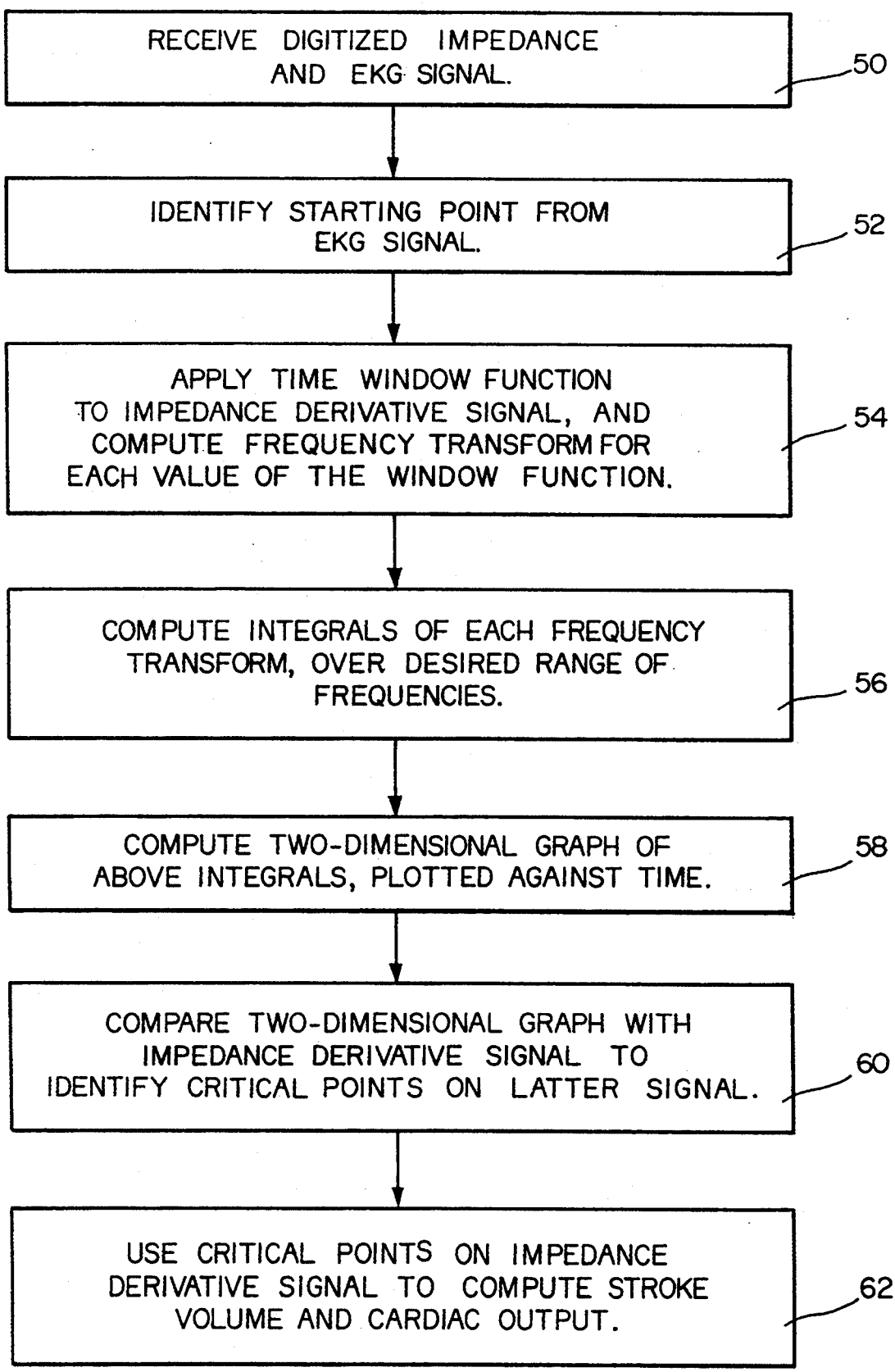
FIG. 7 provides a flow chart illustrating the essential steps of the method of the present invention.

FIG. 7 provides a flow chart showing the essential steps performed by the microprocessor in the present invention. In block 50, the processor receives the digitized impedance and EKG signals. It is assumed that the processor also receives a digitized impedance derivative signal. Alternatively, the processor could digitally differentiate the impedance signal with respect to time, from analysis of the raw data from the impedance measurement.

In block 52, the processor selects a point in time on the EKG signal, and uses this point as the starting reference point for analysis of the impedance derivative signal.

In block 54, the processor calculates frequency transforms for each segment of the impedance derivative signal. To separate the impedance derivative signal into segments, it is convenient to use a time window function. Such a function could have a value of unity over the time interval of interest and a value of zero elsewhere. Other window functions could be used, such as the Hamming window function. The latter function has smoother edges which result in fewer transients or "spikes" in the frequency transform. The Hamming window function otherwise serves the same purpose as the simple step function described above.

One can thus multiply the function to be analyzed (the impedance derivative signal) by the window function, and can then obtain the frequency transform of this product. For each calculation of the frequency transform, the interval over which the window function has a value of unity is changed. Of course, one can accomplish the same result without using a window function, and the invention should not be deemed limited to use of a window function.

In block 56, the processor computes definite integrals of each frequency transform, obtained for each small interval of time. The definite integrals are taken over a frequency range of interest.

In block 58, the processor computes a two-dimensional graph of the above-described definite integrals as a function of time. The computer can transmit the graphical data to the display device, so that the operator can directly compare the graph with a similar graphical representation of the impedance derivative signal. But preferably, the computer will analyze the graphical data automatically to compute the times at which the extreme points B, C, and X (of FIG. 5) occur, as indicated in block 60. The processor then uses these times to compute the maximum excursion of dZ/dt and the ventricular ejection time (VET), from the impedance derivative signal itself. In block 62, the computed parameters are then inserted into the known formulas for stroke volume and cardiac output. If a display or printout of the graphical data are not needed, the processor can do the computations without actually assembling a graph. That is, the processor can simply scan the data to determine the locations of the extrema shown in the example of FIG. 5.

It is apparent that the invention can be varied in many ways. The invention is not limited to a particular frequency transform, for example. While a fast Fourier transform may be preferred, other similar transforms can be used to analyze the data. The placement of electrodes, the arrangement of the computer and peripherals, and other such details can also be varied considerably. The steps of computing transforms, performing definite integrals, assembling a two-dimensional graph, and interpreting that graph could be compressed into fewer steps, especially where the operator does not want or need to see a display of intermediate results. The invention is also not necessarily limited to use in measuring cardiac output. One could analyze other biological signals by the same technique described above. These and other modifications, which will be apparent to those skilled in the art, should be considered within the spirit and scope of the following claims.

What is claimed is:

1. A method of measuring cardiac output of a patient, the method comprising the steps of:
   a) measuring electrical impedance between two locations on the patient, for a predetermined first time interval, thereby obtaining an impedance signal over said first time interval,
   b) differentiating said impedance signal to obtain a signal representative of a first derivative of said impedance signal over said first time interval,
   c) computing a frequency transform of said first derivative of said impedance signal, for each of a plurality of discrete second time intervals, each second time interval being at least an order of magnitude shorter than said first time interval, each of said frequency transforms comprising a function of power versus frequency at one of said second time intervals,
   d) computing a plurality of definite integrals of each of said frequency transforms, the definite integrals being taken over a predetermined range of frequencies,
   e) assembling a graph having an abscissa which comprises time, and an ordinate comprising one of said definite integrals which corresponds to a time represented by the abscissa,
   f) identifying points in time at which extrema appear in the graph produced in step (e), and determining corresponding points in time in said first derivative of said impedance signal,
   g) using said points in the first derivative of said impedance signal to determine a maximum excursion of said first derivative of said impedance signal and to determine a time interval corresponding to ventricular ejection time of the patient, and
   h) calculating cardiac output according to the maximum first derivative of said impedance signal and the ventricular ejection time determined in step (g).

2. The method of claim 1, wherein the frequency transform in step (c) comprises a Fourier transform.

3. The method of claim 1, further comprising the steps of measuring an electrocardiogram of the patient, and using the electrocardiogram to determine a time at which said first time interval begins.

4. A method of measuring cardiac output, the method comprising the steps of:
   a) obtaining a signal corresponding to a first derivative of electrical impedance of a patient, with respect to time,
   b) deriving, for each moment in time, a function which relates intensity of the signal to its frequency, and deriving a graph corresponding to said function,
   c) computing a definite integral of each graph derived in step (b), over a frequency range of interest, and plotting said computed definite integrals as a function of time to form another graph,
   d) comparing extrema of the graph formed in step (c) with the signal obtained in step (a) to identify points on the signal of step (a) which determine a maximum impedance derivative and a ventricular ejection time, and
   e) computing cardiac output from knowledge of the maximum impedance derivative and the ventricular ejection time 5. The method of claim 4, wherein the function derived in step (b) comprises a Fourier transform.

6. The method of claim 4, further comprising the steps of measuring an electrocardiogram of the patient, and using the electrocardiogram to select a time at which the impedance derivative signal is considered to begin.

7. A method of measuring cardiac output of a patient, the method comprising the steps of:
   a) measuring electrical impedance of the patient's body, and computing a first graph of said impedance as a function of time,
   b) computing a plurality of definite integrals of a transform of a signal represented in said first graph, over a frequency range of interest, and deriving a second graph by plotting said definite integrals as a function of time, and
   c) comparing said first graph with said second graph, said second graph having a recognizable pattern of extrema, wherein the extrema of the second graph identify points on the first graph which determine parameters from which one can calculate cardiac output, and using said parameters to calculate cardiac output.

8. The method of claim 7, wherein the transform of step (b) comprises a Fourier transform.

9. The method of claim 7, further comprising the steps of measuring an electrocardiogram of the patient, and using the electrocardiogram to select a time at which said first graph begins.

10. Apparatus for measuring cardiac output of a patient, the apparatus comprising:
    a) means for comparing a first graph derived by measuring electrical impedance of the patient's body, with a second graph having extrema, wherein the extrema of the second graph identify points on the first graph which determine parameters from which one can calculate cardiac output, and means for using said parameters to calculate cardiac output, and
    b) means for plotting a definite integral of a transform of a signal represented in said first graph, over a frequency range of interest, as a function of time, the plotting means having an output, the plotting means including means for connecting said output to the comparing means wherein the second graph is obtained from said means for plotting.

11. The apparatus of claim 10, wherein the comparing means comprises a programmable computer.

12. Apparatus for determining cardiac output of a patient, the apparatus comprising:
    a) at least one pair of electrodes connectable to the patient, a source of electric current connected to the electrodes, and means for determining instantaneous body impedance of the patient connected to the electrodes,
    b) computer means for receiving and processing data from the impedance determining means,
    c) wherein the computer means comprises means for calculating a plurality of frequency transforms of a first derivative of the impedance, for each of a plurality of periods of time, generating a graph formed by plotting definite integrals of said frequency transforms, over a frequency range of interest, against times corresponding to said frequency transforms, comparing the graph with the first derivative of the impedance to determine parameters necessary to calculate cardiac output, and using said parameters to calculate cardiac output.

* * * * *